(12) United States Patent
Vega

(10) Patent No.: US 9,770,525 B2
(45) Date of Patent: Sep. 26, 2017

(54) SUBSTRATE COMPRISING A COMPOSITION REDUCING THE ADHERENCE OF FECES OR MENSES TO THE SKIN

(71) Applicant: The Procter & Gamble Company, Cincinnati, OH (US)

(72) Inventor: Victor Nicholas Vega, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 37 days.

(21) Appl. No.: 14/827,351

(22) Filed: Aug. 17, 2015

(65) Prior Publication Data

US 2015/0352243 A1   Dec. 10, 2015

Related U.S. Application Data

(63) Continuation of application No. 13/417,364, filed on Mar. 12, 2012, now abandoned.

(60) Provisional application No. 61/452,342, filed on Mar. 14, 2011.

(51) Int. Cl.
| | | |
|---|---|---|
| *A61L 15/20* | (2006.01) | |
| *A61Q 19/10* | (2006.01) | |
| *A61K 8/34* | (2006.01) | |
| *C11D 3/37* | (2006.01) | |
| *C11D 17/04* | (2006.01) | |
| *A61L 15/26* | (2006.01) | |
| *A61L 15/34* | (2006.01) | |
| *A61L 15/22* | (2006.01) | |
| *A61Q 19/00* | (2006.01) | |
| *A61K 8/02* | (2006.01) | |

(52) U.S. Cl.
CPC ............ *A61L 15/20* (2013.01); *A61K 8/0208* (2013.01); *A61K 8/345* (2013.01); *A61L 15/225* (2013.01); *A61L 15/26* (2013.01); *A61L 15/34* (2013.01); *A61Q 19/005* (2013.01); *A61Q 19/10* (2013.01); *C11D 3/3707* (2013.01); *C11D 17/049* (2013.01); *Y10T 442/60* (2015.04)

(58) Field of Classification Search
None
See application file for complete search history.

(56) References Cited

U.S. PATENT DOCUMENTS

| | | |
|---|---|---|
| 3,860,003 A | 1/1975 | Buell |
| 4,629,643 A | 12/1986 | Curro et al. |
| 4,695,278 A | 9/1987 | Lawson |
| 4,795,454 A | 1/1989 | Dragoo |
| 4,808,178 A | 2/1989 | Aziz et al. |
| 4,909,803 A | 3/1990 | Aziz et al. |
| 5,968,025 A | 10/1999 | Roe et al. |
| 7,172,801 B2 | 2/2007 | Hoying et al. |
| 7,270,861 B2 | 9/2007 | Broering et al. |
| 7,410,683 B2 | 8/2008 | Curro et al. |
| 7,507,459 B2 | 3/2009 | Turner et al. |
| 7,521,588 B2 | 4/2009 | Stone et al. |
| 7,553,532 B2 | 6/2009 | Turner et al. |
| 7,648,752 B2 | 1/2010 | Hoying et al. |
| 7,670,665 B2 | 3/2010 | Hoying et al. |
| 7,718,243 B2 | 5/2010 | Curro et al. |
| 7,732,657 B2 | 6/2010 | Hammons et al. |
| 7,785,690 B2 | 8/2010 | Turner et al. |
| 2002/0120241 A1* | 8/2002 | Tyrrell ............... A61F 13/8405 604/364 |
| 2006/0140924 A1 | 6/2006 | Stahl et al. |
| 2008/0286320 A1 | 11/2008 | Vega et al. |
| 2009/0155325 A1 | 6/2009 | Wenzel et al. |
| 2012/0238983 A1 | 9/2012 | Vega |

FOREIGN PATENT DOCUMENTS

| | | |
|---|---|---|
| EP | 1992366 A1 | 11/2008 |
| EP | 1992367 A1 | 11/2008 |
| WO | WO97/05908 | 3/1997 |
| WO | WO97/05909 | 3/1997 |
| WO | WO2004/058461 | 7/2004 |
| WO | WO2010/056685 | 5/2010 |
| WO | WO2010/117636 | 10/2010 |

* cited by examiner

*Primary Examiner* — Jianfeng Song
(74) *Attorney, Agent, or Firm* — James T. Fondriest; Kathleen Y. Carter

(57) ABSTRACT

A composition applied on a substrate comprised by, or forming, or used for manufacturing of, a disposable absorbent article may be used for reducing the adherence of feces or menses to the human skin. The composition deposited on the substrate does not affect negatively the manufacturing process of the disposable absorbent article and imparts desirable fluid handling properties to the substrate. The composition may also be desirably deposited on a substrate used as, or in a wipe.

7 Claims, No Drawings

SUBSTRATE COMPRISING A COMPOSITION REDUCING THE ADHERENCE OF FECES OR MENSES TO THE SKIN

FIELD OF THE INVENTION

A composition deposited on a substrate comprised by, or forming, or used for manufacturing of, a disposable absorbent article may be used for reducing the adherence of feces or menses to the human skin. The composition deposited on the substrate does not affect negatively the manufacturing process of the disposable absorbent article and imparts desirable fluid handling properties to the substrate. The composition may also be desirably deposited on a substrate used as, or in a wipe.

BACKGROUND OF THE INVENTION

Disposable absorbent products, such as diapers and sanitary napkins, comprising a composition to deliver skin benefits to the skin of the wearer are known. These compositions can be applied to the topsheet of the absorbent articles, and can be transferred to the skin of the wearer during use. The compositions may provide various skin benefits, such as prevention or treatment of diaper rash.

Over the past years, compositions facilitating feces and/or menses clean up on the skin have also been developed. For instance, disposable absorbent articles comprising a topsheet coated with a composition formulated to reduce the adherence of feces have been developed. Examples of these are disclosed in U.S. Pat. No. 5,968,025, WO 97/05908, WO 97/05909 and US 2006/140924. The disclosed compositions to be applied on topsheets are primarily hydrophobic. Typically, hydrophobic compositions are not preferred since they tend to slow down the transfer of urine from the topsheet to the underlying absorbent cores and also tend to leave an undesirable greasy or slippery feel on the skin. Therefore, hydrophilic compositions have been developed. Examples of these can be found in EP1992366A1 and EP1992367A1 which describe absorbent articles with hydrophilic compositions that transfer to the skin and reduce the adherence of feces or menses to the skin. Though hydrophilic compositions overcoming the above mentioned problems were developed, there was still a need to formulate compositions facilitating feces or menses clean up. Indeed, it was found that some of the hydrophilic compositions of the prior art may incur process problems due to their tendency to remain in a liquid state after deposition onto a substrate for a substantial length of time, thus, affecting negatively the manufacturing process.

It is therefore the purpose of the present invention to provide a substrate used in the manufacture of an absorbent article or in a wipe comprising a composition that exhibits excellent performances at reducing the adherence of feces and/or menses to the skin and that is readily processable.

SUMMARY OF THE INVENTION

The present invention is dedicated to a substrate comprising a composition that reduces the adherence of feces or menses to the skin. The composition is solid at 25° C. and comprises:
(a) from 5% to 95% by weight of an alkoxylated polyol compound;
(b) from 5% to 95% by weight of a structuring agent selected from the group consisting of polyalkylene glycols, polyalkylene glycol derivatives, $C_{14}$-$C_{22}$ fatty alcohols, $C_{12}$-$C_{22}$ fatty acids or their metal salts, waxes and combinations thereof.

The present invention further encompasses a process for manufacturing said substrate and for manufacturing an absorbent article.

The present invention also encompasses a method for reducing the adherence of feces or menses to the human skin which comprises the step of contacting the skin in an area that may be soiled with body exudates with a substrate comprising the composition.

DETAILED DESCRIPTION OF THE INVENTION

As used herein "absorbent article" refers to devices which are intended to be placed against the skin of a wearer to absorb and contain the various exudates discharged from the body. Examples of absorbent articles include incontinence articles such as diapers (infant or adult diapers, pant-like diapers such as training pants), diaper holders or incontinence pads. Further examples of absorbent articles are feminine hygiene products such as sanitary napkins and panty-liners. In a preferred embodiment of the present invention, the absorbent articles are diapers, sanitary napkins and panty-liners.

As used herein "pad-type applicator" refers to devices which are intended to apply a composition to a surface, such as the skin. For instance, the pad-type applicator may have an applicator pad portion having a surface coated with the composition to be dispensed, and an upstanding finger grip portion.

As used herein "body exudates" refers to feces or menses.

As used herein "solid" means that 1 g of the material (e.g. composition), which is placed in the middle of a round glass plate having a diameter of 15 cm, does not run off a glass plate within 1 minute, when the glass plate is tilted at 45°, under conditions of 25° C. and 50% relative humidity. The consistency of the material (e.g. composition) can be measured according to ASTM D5 test method which involves the use of a penetrometer to measure consistency. For instance, by "solid composition" as used herein, it is meant that the composition useful in the present invention has a melting point (100% liquid) above 25° C., or above 30° C., or above 35° C. or above 40° C. With such a melting point, the composition is relatively immobile and remains localized on the substrate at room temperature (e.g. 25° C.).

By body facing surface of a substrate as used herein, it is meant the outer surface or outer surfaces of a substrate that in use are in contact with the skin of the wearer.

Substrate Useful in the Present Invention

The term "substrate" refers to a material suitable for use in an absorbent article, in or as a wipe, or in a pad-like type applicator. When used in an absorbent article, the substrate may be comprised by, or forming, or used for manufacturing of the topsheet and/or the legs cuffs and/or the barrier cuffs and/or the side flaps and/or the side panels and/or the wings of an absorbent article.

Suitable materials include woven and nonwoven materials, film materials and foams. The film materials may be thermoplastic films like apertured formed thermoplastic films, plastic films, apertured plastic films, hydro-formed thermoplastic films, reticulated thermoplastic films. The foams may be porous foams or reticulated foams. Particularly, when used for constituting the pad portion of a pad-like applicator, the substrate may be a flexible, resilient polymeric foam material such as urethane foam, polyethylene foam and the like. Preferred substrates are nonwoven materials and apertured formed thermoplastic films.

"Nonwoven material" as used herein refers to a manufactured web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise two steps: fiber laying onto a forming surface and fiber bonding. The fiber laying step may comprise spunlaying, meltblowing, carding, airlaying, wetlaying, coform and combinations thereof. The fiber bonding step may comprise hydroentanglement, cold calendering, hot calendering, through air thermal bonding, chemical bonding, needle punching, and combinations thereof.

Woven or nonwoven materials may comprise natural fibers or synthetic fibers or combination thereof. Examples of natural fibers may include cellulosic natural fibers, such as fibers from hardwood sources, softwood sources, or other non-wood plants. The natural fibers may comprise cellulose, starch and combinations thereof. The synthetic fibers can be any material, such as, but not limited to, those selected from the group consisting of polyolefins (polypropylene and polypropylene copolymers, polyethylene and polyethylene copolymers), polyesters (e.g., polyethylene terephthalate), polyethers, polyamides, polyesteramides, polyvinylalcohols, polyhydroxyalkanoates, polysaccharides, and combinations thereof. Further, the synthetic fibers can be a single component (i.e. a single synthetic material or a mixture makes up the entire fiber), bi-component (i.e. the fiber is divided into regions, the regions including two or more different synthetic materials or mixtures thereof and may include co-extruded fibers and core and sheath fibers) and combinations thereof. Bi-component fibers can be used as a component fiber of the nonwoven material, and/or they may be present to act as a binder for the other fibers present in the nonwoven material. Any or all of the fibers may be treated before, during, or after manufacture to change any desired properties of the fibers.

The nonwoven material may be a laminate. The laminate may comprise spunbond layer(s) (S), and/or meltblown layer(s) (M), and/or carded layer(s) (C). Suitable laminates include, but are not limited to, SS, SSS, SMS or SMMS.

The substrate useful in the present invention may have a basis weight from about 5 to 100 g/m². Where the substrate is comprised by, or forms, or is used for manufacturing of the topsheet, the legs cuffs and/or the barrier cuffs and/or the side flaps and/or the wings of an absorbent article, it may have for example a basis weight from 5 to 100 g/m², or from about 10 to 40 g/m², or from about 10 to 30 g/m². Where the substrate is used as or in a wipe, it may for example have a basis weight from about 15 to 100 g/m², or from about 30 to 95 g/m², or from about 40 to 85 g/m², or from about 45 to 75 g/m².

The substrate comprises a composition as described in greater details herein below. As the composition limits adherence for body exudates such as feces or menses, it may be comprised in those portions of the substrate comprised by, or forming, or used for manufacturing of the topsheet or the cuffs, which lie adjacent the skin areas of the wearer which typically are contaminated with feces and menses. In some embodiments, at least the body-facing surface of the substrate that in use contacts the skin, such as the body facing surface of the topsheet and/or the legs cuffs and/or the barrier cuffs and/or the side flaps and/or the side panels and/or the wings of the absorbent article, comprises a composition as described herein below.

Compositions Useful in the Present Invention

The compositions useful in the present invention were found to reduce effectively the adherence of feces or menses to the human skin. Such a reduction of the adhesion of feces or menses to the human skin may advantageously facilitate cleansing of the skin, such as the cleansing of the perianal area during a diaper change after a disposable absorbent article comprising the composition has been worn and contacted with the skin. The net result may be that the time and effort required by the individual to achieve a satisfactory state of cleanliness may be minimized. Without being bound by theory, it is believed that the composition may reduce the adhesive force between the soils or exudates and the skin surface because the adhesive forces may be smaller than the cohesive forces within the soils or exudates, thereby allowing the soils or exudates to detach from the skin surface upon application of a shear force (e.g. such as that generated by wiping). Typically, an effective reduction of the adherence of feces and/or menses to the skin is achieved when an average residual ABM of less than 10% as measured by the method described in the Test Method section is obtained.

The transfer or migration of the composition onto the skin from the substrate results in an effective amount of the composition being deposited on the skin. When applied to a substrate comprised by, or forming, or used for manufacturing of, an absorbent article, the compositions are transferable (releasable from the substrate) to the wearer's skin typically by normal contact, wearer motion (thus creating friction), and/or body heat. When applied to a substrate used in, or as a wipe, or when applied to a substrate comprised by the pad portion of a pad-like applicator, the compositions are transferable (releasable from the substrate) to the skin typically by applying a relatively low force to the substrate (e.g. wiping a surface such as the skin in the perianal area with the wipe or rubbing the skin in the perianal area with the product applying surface, i.e. pad portion, of a pad-type applicator). The effective amount of composition that will transfer to the skin will depend on factors such as the type of composition, the portion of the body facing surface of the substrate where the composition is applied, and the type of absorbent article used to administer the composition. An effective amount according to the present invention may be from about 0.0015 mg/cm² (0.01 mg/in²) to about 15.5 mg/cm² (100 mg/in²), preferably from about 0.003 mg/cm² (0.02 mg/in²) to about 12.4 mg/cm² (80 mg/in²), more preferably from about 0.02 mg/cm² (0.15 mg/in²) to about 7.75 mg/cm² (50 mg/in²), of the composition applied to the absorbent article. Typically, an effective amount of the composition of the present invention is applied to an absorbent article such that at least about 0.00015 mg/cm² (0.001 mg/in²) to about 15.5 mg/cm² (100 mg/in²), preferably from about 0.0006 mg/cm² (0.004 mg/in²) to about 11 mg/cm² (72 mg/in²), more preferably from about 0.005 mg/cm² (0.03 mg/in²) to about 6.2 mg/cm² (40 mg/in²), of the composition is transferred to the body during a single use of an absorbent article which is typically about a three hour period. Any suitable method can be used in determining the amount of a composition described herein that is transferred to the body of a wearer during use of an absorbent article containing the composition. Examples of methods for the calculation of transfer amounts of compositions include Gas Chromatographic and other quantitative analytical procedures that involve the analysis of in vivo skin analog materials. A suitable Gas Chromatographic procedure is more fully described in WO 99/45973, Donald C. Roe et al, published Sep. 16, 1999.

The compositions useful in the present invention are solid at 25° C., i.e. they have a melting point (100% liquid) above 25° C. Preferably, the compositions have a melting point (100% liquid) above 30° C., or above 40° C. or above potential "stressful" storage conditions that can be 45° C. or greater. However, the compositions useful in the present invention are flowable (e.g. liquid) at process conditions, e.g. above 50° C. or above 60° C. or above 80° C. or optionally above 100° C.

The compositions suitable for use in the present invention were also found to provide desirable wetting properties to the substrate as a consequence of their hydrophilic nature. For instance, the compositions ensure that liquids (e.g. urine) transfer through the topsheet rapidly. A rapid transfer of urine decreases the likelihood that body exudates will flow off the composition coating rather than being absorbed by the absorbent core. "Hydrophilic" as used herein means that the composition has relatively good water solubility. The water solubility is determined as follows: 100 mg of composition is applied to a glass slide (2.5 cm×8 cm) of known weight, such that the composition covers an area of 2.5 cm×5 cm on the glass slide. The slide is then placed in a beaker containing 75 ml of pure water at room temperature. The water with the composition therein is not stirred. After 4 hours the glass slide is removed from the beaker and put in an oven at 60° C., 5% Relative humidity to remove the water. After drying it is weighted to determine the residual amount of composition on the slide. In one embodiment of the present invention, the composition is considered water soluble if the residual amount of composition on the plate after drying is below 60%, more preferably below 20% and even more preferably below 10%. In one embodiment, compositions having such relatively good water solubility are considered to be hydrophilic within the meaning of the present invention.

Preferably the compositions suitable for use in the present invention are essentially non-aqueous. Non-aqueous means that the compositions either contain no water or they contain water only in minor amounts such as less than 5 wt. % or even less than 1 wt. %. However, these amounts refer to the composition at the time when the absorbent article is produced, i.e. at the time the composition is applied onto the absorbent article. The compositions may be rather hygroscopic, and thus may be able to take up a significant amount of water from the surrounding atmosphere, particularly in an environment with high relative humidity. Thus, when the absorbent article has been stored for a relatively long time, such as several months or even years, it is possible that the amount of water contained in the composition has increased to be more than 5 wt %.

The compositions useful in the present invention are solid at 25° C. and comprise:
(a) from 5% to 95% by weight of an alkoxylated polyol compound,
(b) from 5% to 95% by weight of a structuring agent selected from the group consisting of polyalkylene glycols, polyalkylene glycol derivatives, $C_{14}$-$C_{22}$ fatty alcohols, $C_{12}$-$C_{22}$ fatty acids or their metal salts, waxes and combinations thereof.

Typically, the alkoxylated polyol compound useful in the present invention comprises at least three functional groups independently selected from the group consisting of hydroxyl group or alkoxy group, provided at least one of said functional groups is an alkoxy group. The alkoxy group is preferably a polyalkoxy group selected from the group consisting of polyethoxy, polypropoxy, polybutoxy or mixed poly(ethoxy and/or propoxy and/or butoxy) groups. A polyalkoxy group may comprise from 2 to 200, or from 5 to 180, or from 10 to 80 alkoxy units (i.e. ethoxy, propoxy or butoxy units).

In some embodiments, the alkoxylated polyol compounds may have the general formula $R^1OCH_2$—$(CHOR^2)_n$—$(CHOR^3)_m$—$CH_2OR^4$ wherein $R^1$, $R^2$, $R^3$ and $R^4$ are independently selected from the group consisting of hydrogen, homopolymers of ethylene oxide, propylene oxide or butylene oxide or from copolymers of ethylene oxide, propylene oxide or butylene oxide, provided at least of one of $R^1$, $R^2$, $R^3$ and $R^4$ is not hydrogen and wherein n+m is comprised from 1 to 4. The copolymers of ethylene oxide and/or propylene oxide and/or butylene oxide may include alternating copolymers wherein the monomers are arranged in a regular alternating sequence, periodic copolymers wherein the monomers are arranged in a repeating sequence, random copolymers with random sequences of monomers and block copolymers comprising two or more homopolymer subunits linked by covalent bonds. A copolymer or homopolymer may comprise from 2 to 200, or from 5 to 180, or from 10 to 80 monomers. In some embodiments, the alkoxylated polyol compound comprises in total from 2 to 200, or from 5 to 180, or from 10 to 80 monomers.

The alkoxylated polyol compound may have a melting point ranging from below 30° C., e.g. from 10 to 30° C., to above 30° C., e.g. from 30 to 70° C.

The alkoxylated polyol compound may be derived from a monosaccharide or it may be derived from a disaccharide.

Suitable alkoxylated polyol compounds include, but are not limited to, alkoxylated compounds of sorbitol, maltitol, xylitol, pentaerythritol, mannitol, dulcitol, iditol, glycerol, diglycerol, erythritol, pentaerythritol, lactitol.

The compositions useful in the present invention comprise a total amount of alkoxylated polyol compound ranging from 5% to 95%, or from 20% to 95%, or from 30% to 90%, or from 50% to 80% by weight of the total weight composition. The compositions may comprise a single alkoxylated polyol compound or may comprise a mixture of alkoxylated polyol compounds.

Examples of suitable alkoxylated polyol compounds useful in the present invention include, but are not limited to, PEG-20 sorbitol as available from Abitec Corp. (Janesville, Wis.), PEG-40 sorbitol as available from Croda (Edison N.J.), PEG-50 sorbitol as available from Croda (Edison N.J.), PEG-26 glycerol as available from Abitec Corp. (Janesville, Wis.).

The one or more alkoxylated polyol compound (s), such as described above, is combined with one or more structuring agents selected from the group consisting of polyalkylene glycols, polyalkylene glycol derivatives, $C_{14}$-$C_{22}$ fatty alcohols, $C_{12}$-$C_{22}$ fatty acids or their metal salts, waxes and combinations thereof. The total amount of structuring agent(s) selected from the group consisting of polyalkylene glycols, polyalkylene glycol derivatives, $C_{14}$-$C_{22}$ fatty alcohols, $C_{12}$-$C_{22}$ fatty acids and their metal salts, waxes may range from 5% to 95%, or from 5% to 80%, or from 10% to 70%, or from 20% to 50% by weight of the total weight composition. The structuring agent suitably acts as an agent that impacts positively the processability of the composition, e.g. it increases the crystallization speed of the composition after being melted and applied on a substrate. Additionally or alternatively, the structuring agent may contribute to facilitating the transfer of the composition to the skin. Indeed, if the melting point of the composition (100% liquid) is too high, the composition is not going to transfer efficiently to the skin. The structuring agent can thus be chosen such that the composition has a melting point ensuring transfer of the composition to the skin.

Compositions comprising relatively high percentage of alkoxylated polyol compound, i.e. such as above 50% to 95% by weight of the total weight composition, may be particularly advantageous in that the amount of surfactants in such compositions may be reduced to low level, or the surfactants may even be absent, thus providing surfactant-free compositions. As a result, absorbent articles comprising said compositions are less susceptible to leak when the baby soils the absorbent article.

Suitable structuring agents are described in greater details herein below.

Polyalkylene Glycols

Polyalkylene glycols include polyethylene glycols, either liquid or solid at room temperature, polypropylene glycols, either liquid or solid at room temperature.

Liquid Polyethylene Glycols

Liquid polyethylene glycols as used herein are polyethylene glycols which are liquid at 25° C. They are made from at least 3 units of ethylene glycol and have the general formula HO—(CH2-CH2-O)$_x$—H with x being a number of from 3 to 15 or from 8 to 12. The molecular weight, expressed in Dalton, (weight average) is from 100 to less than 720, preferably from 350 to 700. Typical liquid polyethylene glycols are known as PEG-4, PEG-6, PEG-7, PEG-8, PEG-9, PEG-10, PEG-12 and PEG-14. Suitable trade products are for example Polyglykol 400 of Clariant with an average molecular weight of 380 to 410 or Polyglykol 600 with an average molecular weight of 570 to 630 Daltons.

Liquid Polypropylene Glycol

Liquid polypropylene glycols as used herein are polypropylene glycols which are liquid at 25° C. They are made from at least 3 units of propylene glycol. Typical liquid polypropylene glycols are known as PPG-9, PPG-17, PPG-20, PPG-26 and PPG-30.

Solid Polyethylene Glycol

Solid polyethylene glycols as used herein are polyethylene glycols which are solid at 25° C. They are made from at least 16 units of ethylene glycol and have the general formula HO—(CH2-CH2-O)$_x$—H with x being at least 16, e.g. x is a number of from 16 to 220 or from 40 to 150. The molecular weight, expressed in Dalton, (weight average) is above 720, e.g. from 720 to 100 000, or from 950 to 30 000. Typical solid polyethylene glycols are known as PEG-20, PEG-32, PEG-40, PEG-45, PEG-55, PEG-60, PEG-75, PEG-90 and PEG-100. Suitable trade products are for example Polyglykol 3000 of Clariant with an average molecular weight of 2700 to 3000 or Polyglykol 4000 of Clariant with an average molecular weight of 3700 to 4500 Daltons.

Polyalkylene Glycol Derivatives

Polyalkylene glycol derivatives include polyethylene glycols derivatives, either liquid or solid at room temperature, polypropylene glycols derivatives, either liquid or solid at room temperature. By "derivatives" as used herein, it is meant mono- or di-ester or ether end-capped compounds. The end-capping group(s) may be a methyl, an ethyl, a butyl and/or a propyl group.

Liquid Polyethylene Glycol Derivatives

The liquid polyethylene glycol derivatives as used herein are polyethylene glycol derivatives which are liquid at 25° C. Liquid polyethylene glycol derivatives are mono- or di-ester or ether end-capped polyethylene glycols. The end-capping group(s) may be a methyl, an ethyl, a butyl and/or a propyl group. Suitable liquid polyethylene glycol derivatives include polyethylene glycol monomethyl ether such as available as Polygkycol M400 from Clariant or polyethylene glycol dimethyl ether with a molecular weight of 500 Daltons as available from Sigma-Aldrich.

Liquid Polypropylene Glycol Derivatives

The liquid polypropylene glycol derivatives as used herein are polypropylene glycol derivatives which are liquid at 25° C. The liquid polypropylene glycol derivatives are mono- or di-ester or ether end-capped polypropylene glycols. The end-capping group(s) may be a methyl, an ethyl, a butyl, and/or a propyl group. Suitable liquid polypropylene glycol derivatives include PPG-2 butyl ether, PPG-2 methyl ether, and PPG-3 methyl ether, as available from Dow Chemical (Midland, Mich.).

Solid Polyethylene Glycol Derivatives

Solid polyethylene glycol derivatives as used herein are polyethylene glycol derivatives which are solid at 25° C. They are made from at least 16 units of ethylene glycol, e.g. from 16 to 220 units of ethylene glycol. The solid polyethylene glycol derivatives are mono- or di-ester or ether end-capped polyethylene glycols. The end-capping group(s) may be a methyl, an ethyl, a butyl and/or a propyl group. The molecular weight expressed in Dalton (weight average) is above 720, preferably from 720 to 100000.

Suitable solid polyethylene glycols derivatives include Brij 700 as available from Croda and Myrj 59 as available from Croda.

Solid Polypropylene Glycol Derivatives

Solid polypropylene glycol derivatives as used herein are polypropylene glycol derivatives which are solid at 25° C. They are made from units of propylene glycol. The solid polypropylene glycol derivatives are mono- or di-ester or ether end-capped polyethylene glycols. The end-capping group(s) may be a methyl, an ethyl, a butyl and/or a propyl group.

$C_{14}$-$C_{22}$ Fatty Alcohol, $C_{12}$-$C_{22}$ Fatty Acid and Metal Salts Thereof The fatty compounds, i.e. $C_{14}$-$C_{22}$ fatty alcohol, $C_{12}$-$C_{22}$ fatty acid or metal salts of $C_{12}$-$C_{22}$ fatty acid, are solid at 25° C.

$C_{14}$-$C_{22}$ fatty alcohols consist of an aliphatic hydrocarbon chain of 14 to 22 carbon atoms and a single alcohol group. The aliphatic hydrocarbon chain may be saturated or unsaturated, branched or linear. Preferred fatty alcohols are saturated, linear fatty alcohols. Examples of solid $C_{14}$-$C_{22}$ fatty alcohols include, but are not limited to myristyl alcohol, cetyl alcohol, stearyl alcohol, arachidyl alcohol or behenyl alcohol.

$C_{12}$-$C_{22}$ fatty acids are carboxylic acids with aliphatic hydrocarbon chains. They have from 12 to 22 carbon atoms. The aliphatic hydrocarbon chain may be saturated or unsaturated, branched or linear. Preferred fatty acids are saturated, linear fatty acids. Examples of solid $C_{12}$-$C_{22}$ fatty acids include, but are not limited to, lauric acid, myristic acid, palmitic acid, stearic acid, arachidic acid or behenic acid.

Examples of metal salts of $C_{12}$-$C_{22}$ fatty acid include, but are not limited to, sodium, potassium, lithium, aluminum, magnesium, calcium, manganese, iron, zirconium, cerium, zinc, cobalt or vanadium salts of the above mentioned $C_{12}$-$C_{22}$ fatty acids. Preferred ones are metal salts with low water solubility such as the calcium or magnesium salts, e.g. calcium stearate.

Waxes

The waxes are selected from the group consisting of carnauba, ozokerite, beeswax, candelilla, paraffin, ceresin, esparto, rezowax, isoparaffin and other known mined and mineral waxes.

The alkoxylated polyol compound(s) and structuring agent(s) are selected such that the melting point of the composition (100% liquid) is above room temperature, i.e. above 25° C., in order for the composition to be solid at 25° C.

Suitable combinations of alkoxylated polyol compound(s) and structuring agent(s) include, but are not limited to:

(a) from 5% to 95%, or from 20% to 95%, or from 30 to 90%, or from 50 to 80% by weight of an alkoxylated polyol compound having a melting point below 30° C. and from 5% to 95%, or from 5% to 80%, or from 10% to 70%, or from 20 to 50% by weight of a structuring agent selected from the group consisting of solid polyalkylene glycols or solid polyalkylene glycol derivatives and combinations thereof, or (b) from 5% to 95%, or from 20% to 95%, or from 30 to 90%, or from 50 to 80% by weight of an alkoxylated polyol compound having a melting point above 30° C. and from 5% to 95%, or from 5% to 80%, or from 10% to 70%, or from 20 to 50% by weight of a structuring agent selected from the group consisting of liquid polyalkylene glycols or liquid polyalkylene glycol derivatives and combinations thereof, or (c) from 5% to 95%, or from 20% to 95%, or from 30 to 90%, or from 50 to 80% by weight of an alkoxylated polyol compound having a melting point below 30° C. and from 5% to 95%, or from 5% to 80%, or from 10% to 70%, or from 20 to 50% by weight of a mixture of structuring agents comprising or consisting of:
  a structuring agent selected from the group consisting of solid polyalkylene glycols, solid polyalkylene glycol derivatives and combinations thereof, and
  a structuring agent selected from the group consisting of $C_{14}$-$C_{22}$ fatty alcohols, $C_{12}$-$C_{22}$ fatty acids, metal salts of $C_{12}$-$C_{22}$ fatty acids, waxes and combinations thereof.

In order to ensure both good transferability of the composition to the skin and good processability for the composition (i.e. to ensure that the composition solidifies quickly after application on the substrate to avoid impacting negatively the manufacturing process), it may be preferred to combine an alkoxylated polyol compound melting at above 30° C. with a structuring agent which is liquid at 25° C. or to combine an alkoxylated polyol compound melting at below 30° C. with a structuring agent which is solid at 25° C.

Optional Ingredients

In order to better enhance the benefits to the wearer, additional ingredients can be included in the compositions useful in the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors); fragrances (consumer appeal); humectants (increase the water content of the top layers of the skin); natural moisturizing agents (NMF) and other skin moisturizing ingredients known in the art; opacifiers (reduce the clarity or transparent appearance of the product); skin conditioning agents.

Typically, when present, the optional ingredient(s) may be at a level comprised from 0.03% to 25%, or from 0.05% to 10% or from 0.1% to 5% by weight of the total weight composition.

Method of Depositing the Composition of the Present Invention on a Substrate

The compositions described herein can be applied to a substrate by any known technique for distributing a composition onto a substrate. The composition is typically applied as a melt to a substrate comprised by, or forming, the topsheet and/or the leg cuffs and/or the barrier cuffs and/or the wings and/or the side flaps of a disposable absorbent article or to a substrate used as or, in a wipe. Generally, the composition is applied to the body-facing surface of the substrate. Typically, the composition is heated to a temperature in the range from about 40° to about 100° C., preferably from 50°, or from 60° C., or even from 90° C. to about 100° C. and then applied to the substrate. Non-limiting examples of methods of applying the compositions to a substrate include indirect application such as spraying, or direct application such as printing (e.g., flexographic printing), coating (e.g., contact slot coating and gravure coating), extrusion, or combinations of these application techniques. The composition is then allowed to cool down, i.e. re-solidified, to form a solidified coating on the substrate, generally on its body-facing surface.

The composition may be applied uniformly or non-uniformly to the body facing surface of the substrate. By non-uniform, it is meant here that the amount, pattern of distribution of the composition can vary over the substrate; including for example the embodiment whereby one or more portions of the treated surface of the substrate herein can have a greater amount of composition than other one or more other portions (e.g. some portions comprise a higher basis weight of the composition than other portions, such as for example at least 10% or at least 20% higher), including portions of the surface that do not have composition on them. Where applied non-uniformly, the composition can be applied intermittently, i.e. discontinuously. Any pattern comprising the composition may be utilized, including, for example, application of a pattern of (or a pattern of portion having the shape of) small droplets (obtained via, e.g., spraying), discrete figures of any shape or size, such as round, oval, rectangular, triangular, star-shaped, heart-shaped or shaped in the form of an animal (obtained via, e.g., gravure printing), alternating stripes that run in the longitudinal or lateral direction of the article, etc. By alternating stripes, it is meant portions in which the composition is applied as stripes separated by portions which have no composition applied. Also, the substrate can comprise figures of different shapes and/or of different sizes.

The portions, stripes and/or other discrete figures and/or droplets may have a width from between 0.1 mm, or 0.5 mm, or 2 mm to about 15 mm, or 40 mm, or 50 mm. The spacing between the stripes having no composition applied may have a width from between 0.1 mm, or 0.5 mm, or 2 mm to about 15 mm, or 40 mm or 100 mm. The portions, stripes and/or other discrete figures and/or droplets may have a length of at least 0.5 mm, or of at least 2 mm or of at least 5 mm. In one embodiment, if the portions comprising the composition are in the form of stripes, they may extend from one edge of the substrate to the opposite edge. Preferably, the stripes may extend into the rear waist region of the substrate to the extent that they also cover the buttocks and/or most of the groove length. Where the composition is applied in the form of a pattern of figures, the density and/or the size of the figures and/or the basis weight of the composition comprised by the figures may be higher, such as 10% higher or 20% higher in those portions lying against the areas (e.g., the central third and rear third of the absorbent article) typically affected with feces smeared against the skin.

Disposable Absorbent Articles Comprising the Composition of the Present Invention The compositions described above may be applied to a substrate comprised by, or forming, or used for manufacturing of, a disposable absorbent article. Typically, the compositions are applied to the body facing surface of the substrate.

Diaper

In the following, an infant diaper is described as one embodiment of a disposable absorbent article. However, as the skilled person is aware of, most of the components and materials described herein below are also applicable to other incontinence products such as training pants or adult incontinence products.

The diaper has a longitudinal axis and a transverse axis. The diaper has further an inner, body facing surface and an outer, garment facing surface opposed to the inner surface.

One end portion of the diaper is configured as a front waist region (which is the front one third of the article, having one third of the length of the article). The opposite end portion is configured as a back waist region (back one third) of the diaper, having one third of the length of the article. An intermediate portion of the diaper is configured as a crotch region (centre one third), which extends longitudinally between the front and back waist regions, also having one third of the length of the article. The crotch region is that portion of the diaper which, when the diaper is worn, is generally positioned between the wearer's legs.

The chassis of the diaper comprises the main body of the diaper. The chassis comprises typically a topsheet, which may be liquid pervious, and which may comprise or be made of a substrate comprising a composition as described herein.

The chassis typically also comprises a backsheet, which is generally liquid impervious. In one embodiment, the liquid impervious backsheet comprises a thin plastic film such as a thermoplastic film having a thickness of about 0.01 mm to about 0.05 mm. Suitable backsheet materials comprise typically breathable material, which permit vapors to escape from the absorbent article while still preventing exudates from passing through the backsheet. Suitable backsheet films include those manufactured by Tredegar Industries Inc. of Terre Haute, Ind. and sold under the trade names X15306, X10962 and X10964. The backsheet, or any portion thereof, may be elastically extendable in one or more directions.

The chassis further includes an absorbent core encased between the topsheet and the backsheet. The absorbent core may comprise any absorbent material that is generally compressible, conformable, non-irritating to the wearer's skin, and capable of absorbing and retaining liquids such as urine and other body exudates. The absorbent core may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied, e.g. the absorbent core may have varying caliper zones, a hydrophilic gradient, a superabsorbent gradient, or lower average density and lower average basis weight acquisition zones; or may comprise one or more layers or structures. The total absorbent capacity of the absorbent core should, however, be compatible with the design loading and the intended use of the diaper. Further, the size and absorbent capacity of the absorbent core may be varied to accommodate wearers ranging from infants through adults.

The diaper may also have leg cuffs and/or barrier cuffs, which may comprise or be made of a substrate comprising a composition as described herein. Typically, the diaper may have a pair of opposing (elasticated) leg cuffs, including so-called side panels, and/or a pair of opposing (elasticated) barrier cuffs that provide improved containment of liquids and other body exudates. The cuffs of a pair may be mirror images of one another in the y-axis (longitudinal axis) of the article. Suitable cuffs are described in for example U.S. Pat. Nos. 3,860,003; 4,808,178 and 4,909; U.S. Pat. Nos. 4,695,278 and 4,795,454.

Further, the diaper may comprise a front and back waist band and/or a fastening system, typically joined to the waistband, as known in the art. Preferred fastening systems comprise fastening tabs and landing zones, wherein the fastening tabs are attached or joined to the back region of the diaper and the landing zones are part of the front region of the diaper.

Processes for assembling the diaper include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

Feminine Hygiene Product

In the following, a feminine hygiene product is described (e.g., sanitary napkin or panty-liner). A feminine hygiene product may comprise a topsheet which may comprise or be made of said substrate comprising the composition described herein, a backsheet, and an absorbent core positioned between the topsheet and backsheet. Suitable topsheet are, such as, for example, described in U.S. Pat. Nos. 4,629,643; 7,172,801; 7,270,861; 7,410,683; 7,507,459; 7,521,588; 7,553,532; 7,648,752; 7,670,665; 7,718,243; 7,732,657; 7,785,690; WO 2004/058461 and WO 2010/117636. The backsheet can be any known or otherwise effective backsheet material, provided that the backsheet prevents external leakage of exudates absorbed and contained in the feminine hygiene article. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof, as is well known in the art of making feminine hygiene articles such as sanitary napkins, panty-liners, and the like.

The feminine hygiene product also comprises an absorbent core. The absorbent core is typically positioned between the topsheet and the backsheet. The size and shape of the absorbent core can be altered to meet absorbent capacity requirements, and to provide comfort to the wearer/user. The absorbent core suitable for use in the present invention can be any liquid-absorbent material known in the art for use in absorbent articles, such as the liquid-absorbent materials described herein above.

The feminine hygiene product may also comprise wings which may enable attachment to the underwear of the wearer. The wings may be made of, or comprise a substrate comprising a composition as described herein. The sanitary napkins and/or panty-liners herein may preferably comprise a fastening means comprised by the backsheet and/or by the wings. Preferred are adhesive attachment means that are present on or attached to at least the backsheet.

Wipes Comprising the Composition of the Present Invention

In the following a wipe is described. The wipe may be made of a nonwoven substrate comprising a composition as described herein above. For instance, the composition may be applied, as described herein, to a substrate such as Fibrella 3160, a 58 grams/m$^2$ nonwoven comprising a blend of 40% viscose fibers and 60% polypropylene fibers as available from Suominen of Tampere, Finland.

Whilst not limited to a particular use, the wipe may be intended for cleaning the body, in particular the peri-anal area after defecation and/or the external genital area after urination of babies, toddlers and adults. Other examples of wipes include feminine hygiene wipes.

Method for Reducing the Adherence of Feces or Menses to the Human Skin

The compositions described herein are used for reducing the adherence of feces or menses to the human skin. More particularly, the compositions described herein are beneficial in methods for reducing the adherence of feces or menses to the human skin which comprise the step of contacting the skin in an area that may be soiled with body exudates with a substrate comprising the described composition.

Adherence of fences or menses to the human skin may also be reduced by providing a composition as disclosed herein, applying an effective amount of the composition to the body facing surface of a substrate used in the manufacture of an absorbent article intended to be worn by a wearer (such as the topsheet and/or leg cuffs and/or barrier cuffs and/or side flaps and/or side panels and/or wings), and contacting the skin of the wearer with the absorbent article. By normal contact, wearer motion and/or body heat, the composition transfers to the skin and contributes to reduce the adherence of feces or menses to the skin.

Combinations of Disposable Absorbent Articles and Wipes

The compositions described herein may also be advantageous in methods for improving the cleaning of the skin in areas that may be soiled with body exudates which consider combinations, such as the combined use, of absorbent articles and wipes. For instance, disposable absorbent articles such those described herein (e.g., diaper including a topsheet comprising a substrate comprising a composition as described herein) may be combined with one or more wipes comprising a composition as described herein or with one or more wipes comprising a soil adhering component such as described in WO2010/056685, incorporated herein by reference. The soil adhering compound imparts adherence for body exudates to the wipes. Examples of soil adhering compounds include compounds of formula:

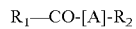

wherein $R_1$ is a $C_{12}$-$C_{22}$ hydrocarbyl or $C_{12}$-$C_{22}$ substituted hydrocarbyl group;

wherein $R_2$ is selected from:
(a) —O—CO—$R_3$ wherein $R_3$ is a $C_{12}$-$C_{22}$ hydrocarbyl or $C_{12}$-$C_{22}$ substituted hydrocarbyl group; or
(b)

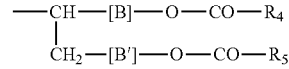

wherein $R_4$ is a $C_{12}$-$C_{22}$ hydrocarbyl or $C_{12}$-$C_{22}$ substituted hydrocarbyl group;
wherein $R_5$ is a $C_{12}$-$C_{22}$ hydrocarbyl or $C_{12}$-$C_{22}$ substituted hydrocarbyl group; wherein A, B and B' are independently selected from:
(a) a polymer or copolymer of ethylene oxide, propylene oxide, butylene oxide, hydroxypropylene oxide wherein said polymer or said copolymer comprises from 2 to 200 monomers, or
(b) —O—$CH_2$—CHOH—$CH_2$—

In the above formula, A, B and B' may be independently selected from polymers of ethylene oxide, propylene oxide, butylene oxide or from copolymers of ethylene oxide, propylene oxide, butylene oxide, hydroxypropylene oxide wherein said polymers or copolymers comprise from 2 to 200 monomers. Copolymers of ethylene oxide and/or propylene oxide and/or butylene oxide and/or hydroxypropylene oxide include alternating copolymers wherein the monomers are arranged in a regular alternating sequence, periodic copolymers wherein the monomers are arranged in a repeating sequence, random copolymers with random sequences of monomers and block copolymers comprising two or more homopolymer subunits linked by covalent bonds. In one embodiment, A, B and B' may be identical.

In the above formula, $R_1$, $R_3$, $R_4$, $R_5$ may be independently selected from $C_{12}$-$C_{22}$ hydrocarbyl or $C_{12}$-$C_{22}$ substituted hydrocarbyl groups. The $C_{12}$-$C_{22}$ hydrocarbyl or $C_{12}$-$C_{22}$ substituted hydrocarbyl groups may be saturated or unsaturated, linear or branched, cyclic or acyclic. In one embodiment $R_1$, $R_3$, $R_4$, $R_5$ may be identical. In another embodiment of the present invention, $R_1$ and $R_3$, or $R_1$, $R_4$ and $R_5$ may be independently selected from the group consisting of $C_{12}$-$C_{22}$ alkyl, alkenyl, hydroxyalkyl or alkoxyl group.

Absorbent articles comprising a soil adhering component such as described above or in WO2010/056685 may also be combined with one or more wipes comprising a composition as described herein. Advantageously, the cleansing of the skin during a diaper change may be facilitated by such a combination. The wipe deposits on the skin in the perianal area a composition which reduces the adherence of feces to the skin whilst the subsequently worn diaper exhibits adherence for feces. As a result of the combination, less soil adheres to the skin and more soil adheres to the disposable absorbent article, facilitating the cleansing of the skin at the time of the next diaper change.

These combinations include combined uses or sales. The absorbent articles comprising a substrate comprising the composition as described herein may be packaged with one or more wipes. In one embodiment, one or more wipes may be packaged in a first package and one or more absorbent articles may be packaged in a second package. The first and second packages may be packaged together or they may be held in assembly by any means. In another embodiment, one absorbent article may be packaged with one or more wipes as one individual package, which is especially convenient for users en-route, where it might be desirable to carry only one absorbent article and one or more wipes. The absorbent articles and the wipes may also be co-marketed, e.g., designed and/or advertised to be sold and/or used together.

EXAMPLES

The following compositions were prepared by combining the following melted (i.e., liquid) components together. Their ability to reduce the adherence of feces to the skin (anti-stick performance) was investigated according to the skin adherence test method described below with the artificial bowel movement lotion as described below. The results are summarized in the table below. An average residual AMB of less than 10% is illustrative of highly beneficial anti-stick performance.

| Compositions | Average Residual ABM (%) |
|---|---|
| — | 31% |
| PEG-20 Sorbitol[1]/PEG 4000[2] (50/50) | 2% |
| PEG-40 Sorbitol[3]/PEG-90 monobutyl ether[4]/stearyl alcohol[5] (88/6/6) | 1% |
| PEG-50 Sorbitol[6]/PEG-90 monobutyl ether[4] (70/30) | 2% |
| PEG-50 Sorbitol[6]/PEG-4000[2] (70/30) | 3% |
| PEG-40 Sorbitol[3]/PEG-4000[2]/Stearyl alcohol[5] (90/5/5) | 4% |

[1]supplied by Abitec Corp. (Janesville, WI)
[2,4]supplied by Sasol North America (Houston, TX)
[3,6]supplied by Croda (Edison, NJ)
[5]supplied by the Procter & Gamble Company (Cincinnati, OH)

Test Methods

Skin Adherence Test Method

This method may be used for assessing the adhesion of soils or exudates to a substrate by quantifying the percentage of residual artificial pasty bowel movement ("ABM") left on a transparency film after application of a composition treatment on the transparency film. The ABM, similar to real infant bowel movement, fails cohesively, resulting in part of the ABM remaining on the transparency film and part of the ABM being removed. The more efficient the composition is, the lower is the percentage of residual ABM on the transparency film.

The transparency film that is used is part # CEB00559 Transparency Film For Copiers, supplied by Corporate Express (Broomfield, Colo.). A sheet of transparency film is placed on a flat horizontal surface, such as a table or bench, and the film is anchored on the top and bottom to the flat surface using adhesive tape.

A template and a fine-tip marker are used to mark-off up to twelve 3 cm by 3 cm sites on individual sheets of the transparency film, i.e. up to twelve sites per sheet of film. For each composition tested, three transparency film sites are treated with the composition. Three sites also receive no treatment, i.e. serves as a negative control. The locations of the various treatments, including the no-treatment sites, may be randomized among the sites on the transparency films. For each site that is treated, a predetermined amount of 200-400 µg/cm² of the composition is applied in the center of the site with a powder-free finger cot, Catalog #56613-413 as available from VWR Scientific of West Chester, Pa. The applied composition is then spread over the entire site (the boundary of which is defined by the marks made using the template) using the powder-free finger cot, by placing the finger cot on top of the agent or composition and lightly rubbing the finger cot over the skin surface using several side-to-side and up-and-down movements for a total elapsed time of 10 seconds. Examining the site from an oblique angle, the person conducting the test needs to ensure that a uniform film has been formed over the entire area of the site. The film is left exposed to air, untouched, for approximately 1 minute prior to proceeding with the subsequent steps.

A 1 ml syringe, such as Catalog # BD-309628 as available from VWR Scientific of West Chester, Pa., that has been filled with room temperature ABM and is devoid of air bubbles, is placed onto a tared four-place analytical balance. The weight is recorded. The syringe with ABM is held over the center of the test site on the transparency film, approximately 2 mm from the transparency film surface, and approximately 0.2 mL of ABM is dispensed onto the transparency film by pressing the plunger and by watching the gradations on the syringe. The ABM should form a uniform, compact mound in the center of the test site. The syringe is re-weighed on the analytical balance, and the weight is recorded. The quantity of ABM that was delivered to the transparency film is calculated by subtracting the second weight from the first.

A 4 cm×4 cm piece of weigh paper, Catalog #12578-201 as available from VWR Scientific of West Chester, Pa., is tared on the four place analytical balance, centered over the ABM mound on the transparency film test site, and gently lowered onto the ABM using forceps. The weigh paper must not be touched with fingertips, as this may transfer oils onto its surface. Next, a 500 g bottle-shaped weight, such as Catalog #12766-518 as available from VWR Scientific of West Chester, Pa., that exerts approximately 0.5 psi of downward force is placed over the weigh paper such that the mound of ABM under the weigh paper is approximately centered under the weight. After 30 seconds have elapsed, the 500 g weight is slowly lifted. Using a pair of forceps, the weigh paper is slowly and gently peeled from the test site. The forceps are placed at the lower right corner of the weigh paper, and the weigh paper is slowly peeled upwards in the direction of the upper left corner of the weigh paper. It should take approximately 1-2 seconds to remove the weigh paper. Once removed, the weigh paper is placed back onto the analytical balance that it was tared on, and the weight is recorded to determine the amount of ABM removed.

The above steps are repeated until all sites on the transparency films have been tested, i.e. the steps consisting of application of composition, application of ABM, application of weigh paper, application of weight, and removal of weigh paper. For the no-treatment control, application of agent or composition is omitted and ABM is applied directly to the transparency film. The weight percent (%) residual ABM left on the transparency film after treatment is calculated from the weight measurements according to the equation $$((\text{ABM Applied} - \text{ABM Removed})/\text{ABM Applied}) \times 100.$$

The mean value for residual ABM and standard error of the mean for each composition is calculated. When the method is run correctly, the no treatment control typically yields a value between approximately 30% to 50% residual ABM. To ensure reproducible results, the Skin adherence Method should be run at a room temperature of 21° C.±2° C. and at a relative humidity of 30-50%.

Preparation of Artificial Pasty Bowel Movement (ABM)
The following equipment is required:
an analytical balance accurate to ±0.001 g
a homogenizer capable of stirring the ingredients to homogeneity, such as an Ika Labortechnik™ T25 basic or equivalent as available from Ika-Werke GmbH and Co. KG of Staufen, Germany.

a homogenizer probe to be used with the homogenizer, such as Catalog # S25N 25F as available from Ika-Werke GmbH and Co. KG of Staufen, Germany.

The following reagents are required:

Feclone™ Powder #4, available from SiliClone Studio, Valley Forge, Pa., as Catalog Number Feclone BFPS-4.

Feclone™ Powder #6, available from SiliClone Studio, Valley Forge, Pa., as Catalog Number BFPS-6.

Feclone™ Powder #7, available from SiliClone Studio, Valley Forge, Pa., as Catalog Number BFPS-7.

Carbopol™ 981, available from Noveon, Cleveland, Ohio

Deionized water.

The following quantities of the above reagents are required:

| Ingredient | Grams |
| --- | --- |
| Deionized water for Carbopol™ solution | 78.78 |
| Feclone™ powder #4 | 6.600 |
| Feclone™ powder #6 | 6.600 |
| Feclone™ powder #7 | 6.600 |
| Carbopol™ 981 | 0.900 |

The procedure to prepare the ABM consists of the following steps:

A. Preparation of Carbopol™ Solution

1. Weigh 78.78 g±0.01 g of deionized water in a 250 ml beaker.
2. Weigh 0.900 g±0.001 g of Carbopol™ on weigh paper.
3. Put beaker on a magnetic stirrer and set speed at 400 rpm.
4. Add Carbopol™ powder slowly to the water, over the span of about 5 minutes. While adding the Carbopol™, increase the stirring speed slowly to 600 rpm.
5. Once the Carbopol™ powder has been added to the water, cover the beaker and continue mixing at 600 rpm for 15 minutes. The Carbopol™ powder must be completely dispersed, i.e. a transparent gel without any agglomerates.
6. Set up a hot plate at 150° C. Place the Carbopol™ solution on the hot plate and continue mixing at 600 rpm until the solution is heated to 81° C. to 83° C.

B. Preparation of ABM Mixture

1. Weigh 6.600 g±0.01 g each of Feclone powders #4, #6, and #7 into a beaker and mix well.
2. Using a T25 basic or equivalent homogenizer with a homogenizer probe, stir the Carbopol™ solution at 8000 rpm for about 30 seconds before proceeding with Step 3.
3. To the Carbopol™ solution that is being stirred, slowly add the Feclone™ powder mixture, about one quarter of the total at a time. Ensure that the Feclone™ powder mixture gets pulled through the homogenizer probe during addition, i.e. is thoroughly mixed into the pasty composition that is forming. If necessary, use a spatula to facilitate incorporation of the Feclone™ powder mixture into the composition.
4. After all of the Feclone™ powder mixture has been added, continue mixing with the homogenizer at 8000 rpm for an additional 5 minutes, using the spatula to push the pasty composition towards the homogenizer probe. The composition should be thoroughly mixed and appear homogeneous.

The finished ABM may be placed in a container, such as Catalog #14233-954 as available from VWR Scientific of West Chester, Pa., and stored in the refrigerator for up to 30 days. After 30 days, a new sample should be prepared for further experiments. The container must be tightly sealed to avoid drying out of the ABM. Prior to using the ABM in the Skin Adherence Method, the ABM must be removed from the refrigerator and allowed to adjust back to room temperature. An easy way to accomplish this is to fill a 10 ml syringe, such as Catalog # BD301604 as available from VWR Scientific of West Chester, Pa., with cold ABM and then allow the syringe to equilibrate to room temperature on a counter top. Equilibration typically takes about 15 minutes. The 10 ml syringe can then be used to fill the 1 ml syringe described in the Skin adherence Test Method.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a substrate comprising an anhydrous composition, wherein said composition is solid at 25° C. and comprises:

(a) from 5% to 95% by weight of an alkoxylated polyol compound, wherein the alkoxylated polyol is selected from the group of alkoxylated sorbitol, alkoxylated maltitol, alkoxylated xylitol, alkoxylated mannitol, alkoxylated dulcitol, alkoxylated iditol, alkoxylated diglycerol, alkoxylated erythritol, alkoxylated pentaerythritol and combinations thereof;

(b) from 5% to 95% by weight of a structuring agent selected from the group consisting of polyalkylene glycols, polyalkylene glycol derivatives, $C_{14}$-$C_{22}$ fatty alcohols, $C_{12}$-$C_{22}$ fatty acids and their metal salts, waxes and combinations thereof.

2. The substrate according to claim 1 wherein said alkoxylated polyol compound has the formula $R^1OCH_2$—$(CH_2OR^2)_n$—$(CH_2OR^3)_m$—$CH_2OR^4$ wherein $R^1$, $R^2$, $R^3$ and $R^4$ are independently selected from the group consisting of hydrogen, homopolymers of ethylene oxide, propylene oxide and butylene oxide and from copolymers of ethylene oxide, propylene oxide and butylene oxide provided at least of one of $R^1$, $R^2$, $R^3$ and $R^4$ is not hydrogen and wherein n+m is comprised from 1 to 4.

3. The substrate according to claim 1 wherein said composition comprises at least 50% by weight of said alkoxylated polyol compound and at most 50% by weight of said structuring agent.

4. The substrate according to claim 1 wherein said alkoxylated polyol compound has a melting point below 30° C. and wherein said structuring agent is selected from the group consisting of solid polyalkylene glycols, solid polyalkylene glycol derivatives and combinations thereof.

5. The substrate according to claim 1 wherein said alkoxylated polyol compound has a melting point above 30° C. and wherein said structuring agent is selected from the group consisting of liquid polyalkylene glycols, liquid polyalkylene glycol derivatives and combinations thereof.

6. The substrate according to claim 1 wherein said alkoxylated polyol compound has a melting point below 30° C. and wherein the composition comprises a mixture of structuring agents comprising:

a structuring agent selected from the group consisting of solid polyalkylene glycols, solid polyalkylene glycol derivatives and combinations thereof, and a structuring agent selected from the group consisting of $C_{14}$-$C_{22}$ fatty alcohols, $C_{12}$-$C_{22}$ fatty acids, metal salts of a $C_{12}$-$C_{22}$ fatty acids, waxes and combinations thereof.

7. The substrate of claim 1 wherein said substrate is a nonwoven material or a film.

* * * * *